United States Patent [19]
Rei et al.

[11] Patent Number: 5,498,344
[45] Date of Patent: Mar. 12, 1996

[54] LOW-TEMPERATURE-STABILIZED ISOTHIAZOLINONE CONCENTRATES

[75] Inventors: Nuno M. Rei, Boxford; Roger G. Hamel, Methuen, both of Mass.

[73] Assignee: Morton International, Inc., Chicago, Ill.

[21] Appl. No.: 382,729

[22] Filed: Feb. 2, 1995

[51] Int. Cl.$^6$ .................. A01N 43/80; C07D 275/03; C09K 15/30
[52] U.S. Cl. ................................ 252/404; 548/213
[58] Field of Search ........................ 252/404; 548/213

[56] References Cited

U.S. PATENT DOCUMENTS

| | | | |
|---|---|---|---|
| 3,360,431 | 12/1967 | Yeager | 167/30 |
| 4,663,077 | 5/1987 | Rei et al. | 252/364 |
| 4,761,247 | 8/1988 | Rei et al. | 252/364 |
| 5,028,619 | 7/1991 | Rei et al. | 514/372 |

FOREIGN PATENT DOCUMENTS 2138798  10/1984  United Kingdom.

*Primary Examiner*—Johann Richter
*Assistant Examiner*—Laura R. Cross
*Attorney, Agent, or Firm*—Wayne E. Nacker; Gerald K. White

[57] ABSTRACT

A liquid concentrate comprises between about 4 and about 25 wt % of an isothiazolinone compound or mixture of isothiazolinone compounds between about 25 and about 88 wt % of a plasticizer in which said isothiazolinone compound is soluble and between about 8 and about 50 wt % of a $C_6$-$C_{12}$ monoalkylphenol(s) which stabilizes the concentrate against crystallization and/or freezing at sub-freezing conditions.

9 Claims, No Drawings

LOW-TEMPERATURE-STABILIZED ISOTHIAZOLINONE CONCENTRATES

The present invention is directed to liquid concentrates of isothiazolinones, which concentrates are stable to crystallization or freezing at sub-freezing temperatures.

BACKGROUND OF THE INVENTION

It is well known to add biocides to thermoplastic resin compositions to protect articles formed from such compositions against microbial degradation. For processing reasons, it is known to provide biocides as concentrates, such as liquid concentrates as taught, for example, in U.S. Pat. No. 4,758,609, or solid concentrates as taught, for example, in U.S. Pat. No. 4,086,297, the teachings of each of which are incorporated herein by reference. Although a number of biocides have been suggested for use in thermoplastic resins, including isothiazolinones, the standard anti-microbial agent in the industry has been and remains 10,10'-oxybisphenoxarsine (OBPA). While OBPA has proven to be a very effective biocide for use in the plastics industry, there is perceived an eventual need to replace OBPA due to its heavy metal (arsenic) content.

Isothiazolinone compounds are one class of biocides considered to be effective replacements for OBPA and similar heavy metal-containing biocides. At room temperature, some isothiazolinone compounds are in solid form and therefore difficult to handle. Such solid isothiazolinones may be more easily handled if dissolved in a liquid carrier, such as a plasticizer. Even if the isothiazolinone is in liquid form at room temperature, it is often desirable to dilute the isothiazolinone with a carrier to minimize mixing problems. Accordingly, liquid isothiazolinone, concentrates, have been prepared, as taught, for example, in U.S. Pat. No. 5,028,619.

The carrier for a liquid concentrate preferably is a liquid that also has a function in the end-use resin composition to which the concentrate is added so as to provide anti-microbial properties, and typically in liquid concentrates the carrier is a plasticizer for the end-use resin composition. A problem with concentrates of isothiazolinone-in-plasticizer concentrates wherein the isothiazolinone is present in amounts of greater than about 4 wt %, particularly in amounts of about 10 wt % or greater, is that in sub-freezing conditions which the concentrate may encounter if shipped or stored in winter, the isothiazolinone compounds tend to crystallize from solution or the entire concentrate solution tends to freeze. This is a significant inconvenience for the plastic processor who must wait for the isothiazolinone to redissolve or the concentrate to thaw and then make sure that the concentrate is homogeneous.

It is a general object of the present invention to provide isothiazolinone concentrates which are stable to crystallization and/or freezing in winter shipping and storage conditions.

SUMMARY OF THE INVENTION

As one aspect of the invention, a liquid concentrate comprises between about 4 and about 25 wt %, preferably at least about 10 wt %, of an isothiazolinone compound, between about 25 and about 88 wt % of a plasticizer(s) in which said isothiazolinone compound is soluble, and between about 8 and about 50 wt % of a $C_6$-$C_{12}$ monoalkylphenol(s). The monoalkylphenol stabilizers the concentrate against crystallization and/or freezing at sub-freezing conditions.

In accordance with another aspect of the invention, there is provided a solution of an isothiazolinone compound in a $C_6$-$C_{12}$ monoalkylphenol(s). If this solution is intended to be added directly to a thermoplastic resin composition, the isothiazolinone compound is present at a level of between about 4 and about 25 wt %. If the solution is to be used as an intermediate for forming a isothiazolinone/plasticizer/monoalkylphenol concentrate, the isothiazolinone compound will be present at a level of at least about 20 wt % up to its limit of solubility.

DETAILED DESCRIPTION OF CERTAIN PREFERRED EMBODIMENTS

Herein, it is to be understood that when any class of compound is discussed in the singular, unless otherwise indicated, a mixture of such compounds may be used instead. Thus, when the term "isothiazolinone compound" is used in the singular, a mixture of "isothiazolinone compounds" is within the scope of the invention; when the term "alkyl phenol" is used, a mixture of "alkyl phenols" is in accordance with the invention; and when the term "plasticizer" is used, it is to be understood that a mixture of "plasticizers" would be in accordance with the invention.

Generally any plasticizer in which the isothiazolinone compound is soluble is suitable for forming a concentrate in accordance with the present invention. Examples of such plasticizers include, but are not limited to tricresyl phosphate, dipropylene glycol dibenzoate, diphenylcresyl phosphate, dipropylene glycol dibenzoate, diphenylcresyl phosphate, epoxidized soya, epoxidized tallate, dioctyl azelate, di(2-ethyl hexyl)phthalate, alkyl aryl phosphates, diisobutyl phthalate, diisodecyl phthalate, hydrogenated methyl rosin ester, n-octyl n-decyl phthalate, mixed n-alkyl phthalates, butyl benzyl phthalate, di-n-octyl phthalate, di-n-decyl phthalate, 3,4-epoxycyclohexyl methyl 3,4-epoxycyclohexane carboxylate, trioctyl trimellitate and low molecular wight polymeric plasticizers such as Paraplex® G-30 plasticizer sold by Rohm & Haas Co. and the like. Of these plasticizers, di(2-ethyl hexyl) phthalate, diisodecyl phthalate, butyl benzyl phthalate and epoxidized soya are preferred.

The isothiazolinone compounds useful in this invention include those described in U.S. Pat. Nos. 3,523,121 (issued Aug. 4, 1970); 3,761,488 (issued Sep. 25, 1973) and 4,105,431 (issued Aug. 8, 1978). The isothiazolinone compounds described in these patents have the structural formula:

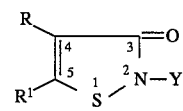

wherein Y is alkyl of 1 to 18 carbon atoms, preferably 3 to 18 carbon atoms; cycloalkyl of 3 to 6 carbon atoms; aralkyl of up to 10 carbon atoms; halogen, lower alkyl, or lower alkoxy substituted aralkyl of up to 10 carbon atoms; aryl; halogen, nitro, lower alkyl, lower alkylacylamino, lower carbalkoxy or sulfamyl substituted aryl; lower hydroxyalkyl; lower haloalkyl; lower dialkylaminoalkyl; or a carbamoyl group having the structure

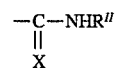

When Y is any of the above substituents other than the carbamoyl group, then R and R' may be hydrogen, halogen or lower alkyl, provided that when Y is methyl or ethyl then both R and $R^I$ may not be hydrogen.

When Y is the carbamoyl group, then R may be hydrogen, lower alkyl, halogen or cyano;

$R^I$ may be hydrogen, halogen, lower alkyl or lower haloalkyl when R is hydrogen, lower alkyl or halogen;

$R^I$ may be lower alkylthio, lower alkylsulfinyl or lower alkylsulfonyl when R is cyano;

X may be oxygen or sulfur; and $R^{II}$ may be alkyl of 1 to 18 carbon atoms, lower alkylsulfonyl, arylsulfonyl, halogen or lower alkyl substituted arylsulfonyl, carbalkoxyalkyl of the structure

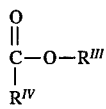

where $R^{III}$ is lower alkyl and $R^{IV}$ is an alkylene group of 1 to 4 carbon atoms, or $R^{II}$ may be an aryl group of the formula

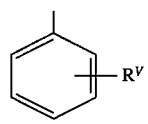

wherein $R^V$ may be lower alkyl, halogen, nitro or alkoxy or 1 to 4 carbon atoms.

Where the expression "lower" is employed in conjunction with terms, such as alkyl, haloalkyl, alkylthio, alkylsulfinyl, alkylsulfonyl, etc., it is intended to indicate that the alkyl or alkyl portion thereof has a carbon content of 1 to 4 carbon atoms. Typically, the alkyl or alkyl portion may be methyl, ethyl, propyl, isopropyl, butyl, t-butyl and the like.

Some of the isothiazolinones described above can form novel acid salts which also exhibit biocidal activity. Such salt forming compounds fall within the scope of the above formula wherein Y is alkyl of 1 to 18 carbon atoms; cycloalkyl of 3 of 6 carbon atoms; aralkyl of up to 10 carbon atoms; halogen lower alkyl, or lower alkoxy substituted aralkyl of up to 10 carbon atoms; aryl; halogen, nitro, lower alkyl, lower alkylacylamino, lower carbalkoxy or sulfamyl substituted aryl; lower hydroxyalkyl; lower haloalkyl; or lower dialkylaminoalkyl; and R and $R^I$ are selected from the group consisting of hydrogen, lower alkyl, or halogen.

Some examples of isothiazolinone compounds useful in accordance with the invention include, but are not limited to:

2-(n-octyl-4-isothiazolin-3-one),
4,5-dichloro-2-cyclohexyl-3-isothiazolinone,
4,5-dichloro-2-(n-octyl-4-isothiazolin-3-one)
5-chloro-2-methyl-4-isothiazolin-3-one,
2-methyl-4-isothiazolin-3-one, and mixtures thereof.

The freezing/crystallization problem discussed above occurs especially when the isothiazolinone compound or one of the isothiazolinone compounds has a melting point of 30° C. or above. Of particular interest in this regard is 4,5-dichloro-2-(n-octyl-4-isothiazolin-3-one) which has a melting point of above 40° C. This compound, exhibits improved stability (weatherability) relative to other isothiazolinone compounds heretofore used as biocides, such as liquid 2-(n-octyl-4-isothiazolin- 3-one), in outdoor conditions. Thus, the desire to provide concentrates of this compound. However, concentrates of this solid biocide compound tend to freeze or crystallize.

While isothiazolinone concentrates containing biocides are useful for imparting antimicrobial activity to many thermoplastic resin compositions, rigid thermoplastic compositions must be substantially plasticizer-free. Accordingly, solutions of isothiazolinone compound in $C_6$-$C_{12}$ monoalkylphenol solutions are within the scope of the invention. Also, such solutions may be formed as an intermediate for isothiazolinone/plasticizer/monoalkylphenol concentrates.

Of the $C_6$-$C_{12}$ monoalkylphenols useful in the invention, nonylphenol is currently preferred from the standpoint of availability and cost. Nonylphenol is a mixture of isomers, predominantly para.

It is also within the scope of this invention to use mixtures of biocides that include an isothiazolinone and another biocide, such as OBPA, discussed above.

The invention will now be described in greater detail by way of specific examples.

EXAMPLES 1–12

Samples with various amounts of 4,5-dichloro-2-(n-octyl-4-isothiazolin-3-one) (RH 287), plasticizer and nonylphenol (np) were exposed to temperatures of 0° F. (−18° C.) for 48 hours and the samples then observed. Compositions (components in wt %; plasticizer=balance) and results are as follows:

| Example | RH287 | Plasticizer | Stabilizer | Comments |
|---|---|---|---|---|
| 1 | 5 | DIDP | 0 | OK |
| 2 | 5 | DOP | 0 | OK |
| 3 | 7.5 | DIDP | 0 | Frozen |
| 4 | 10 | DOP | 0 | Frozen |
| 5 | 10 | DIDP | 20 np | OK |
| 6 | 10 | DOP | 20 np | OK |
| 7 | 20 | DIDP | 40 np | OK |
| 8 | 20 | DOP | 40 np | OK |
| 9 | 20 | S160 | 40 np | OK |
| 10 | 20 | S711 | 40 np | OK |
| 11 | 7.5 | S160 | 0 | OK |
| 12 | 10 | S160 | 0 | Frozen |

DIDP = diisodecylphthalate
DOP = di 2-ethyl hexyl phthalate
S160 = butyl benzyl phthalate
S711 = predominantly straight chain phthalate ester The above-examples show a general trend that nonylphenol enhances the low temperature stability of a concentrate of the solid biocide in plasticizer. Although some of the examples, i.e., 1, 2 and 11, contained no stabilizer and nevertheless were "OK" after the 48 hour freeze, it is to be appreciated that biocide concentrates may be exposed during shipping and storage to even lower temperatures.

What is claimed is:

1. A liquid concentrate comprising between about 4 and about 25 wt % of an isothiazolinone compound or mixture of isothiazolinone compounds, between about 25 and about 88 wt % of a plasticizer in which said isothiazolinone compound or mixture of isothiazolinone compounds is soluble and between about 8 and about 50 wt % of a $C_6$-$C_{12}$ monoalkylphenol(s).

2. A liquid concentrate according to claim 1 wherein said monoalkylphenol is nonylphenol.

3. A liquid concentrate according to claim 1 comprising an isothiazolinone compound having a melting temperature of about 30° C. or above.

4. A liquid concentrate according to Claim 1 wherein said isothliazolinone compound is selected from the group consisting of:

2-(n-octyl-4-isothiazolin-3-one),
4,5-dichloro-2-cyclohexyl-3-isothiazolinone,
4,5-dichloro-2-(n-octyl-4-isothiazolin-3-one)

5-chloro-2-methyl-4-isothiazolin-3-one, 2-methyl-4-isothiazolin-3-one, or mixtures thereof.

5. A liquid concentrate comprising between about 4 and about 25 wt % of 4,5-dichloro-2-(n-octyl-4-isothiazolin-3-one), between about 25 and about 88 wt % of a plasticizer in which said 4,5-dichloro-2-(n-octyl-4-isothiazolin-3-one) is soluble and between about 8 and about 50 wt % of a $C_6$-$C_{12}$ monoalkylphenol(s).

6. A solution comprising between about 4 and about 25 wt % of an isothiazolinone compound or mixture of isothiazolinone compounds in a $C_6$-$C_{12}$ monoalkylphenol.

7. A solution comprising at least 20 wt % of an isothiazolinone compound or mixture of isothiazolinone compounds.

8. A solution according to claim 6 wherein said monoalkynolphenol is nonylphenol.

9. A solution according to claim 6 wherein said isothiazolinone compound is selected from the group consisting of:

2-(n-octyl-4-isothiazolin-3-one), 4,5-dichloro-2-cyclohexyl-3-isothiazolinone, 4,5-dichloro-2-(n-octyl-4-isothiazolin-3-one)

5-chloro-2-methyl-4-isothiazolin-3-one, 2-methyl-4-isothiazolin-3-one, or mixtures thereof.

* * * * *

UNITED STATES PATENT AND TRADEMARK OFFICE
CERTIFICATE OF CORRECTION

PATENT NO. : 5,498,344
DATED : March 12, 1996
INVENTOR(S) : Rei et al.

It is certified that error appears in the above-indentified patent and that said Letters Patent is hereby corrected as shown below:

Col. 5, line 15 of the patent, before the ending period (.), insert -- in a $C_6$-$C_{12}$ monoalkylphenol --

Signed and Sealed this

First Day of April, 1997

Attest:

BRUCE LEHMAN

Attesting Officer

Commissioner of Patents and Trademarks